(12) United States Patent
Pan et al.

(10) Patent No.: US 9,233,954 B2
(45) Date of Patent: Jan. 12, 2016

(54) ORGANIC AMINE SALTS OF AZILSARTAN, PREPARATION METHOD AND USE THEREOF

(75) Inventors: Bigao Pan, Jiangsu (CN); Longbin Huang, Jiangsu (CN); Baohai Yang, Jiangsu (CN)

(73) Assignees: Jiangsu Hansoh Pharmaceutical Co., Ltd., Lianyungang, Jiangsu (CN); Jiangsu Hansoh Pharmaceutical Group Co., Ltd., Lianyungang, Jiangsu (CN); Jiangsu Hansoh Medicine Institute Co., Ltd., Lianyungang, Jiangsu (CN)

( * ) Notice: Subject to any disclaimer, the term of this patent is extended or adjusted under 35 U.S.C. 154(b) by 240 days.

(21) Appl. No.: 13/979,931

(22) PCT Filed: Jan. 11, 2012

(86) PCT No.: PCT/CN2012/070219
§ 371 (c)(1),
(2), (4) Date: Jul. 16, 2013

(87) PCT Pub. No.: WO2012/097697
PCT Pub. Date: Jul. 26, 2012

(65) Prior Publication Data
US 2013/0296334 A1    Nov. 7, 2013

(30) Foreign Application Priority Data

Jan. 20, 2011    (CN) .......................... 2011 1 0022311

(51) Int. Cl.
| | | |
|---|---|---|
| *C07D 413/10* | (2006.01) | |
| *A61K 31/4245* | (2006.01) | |
| *C07C 213/08* | (2006.01) | |
| *C07C 215/08* | (2006.01) | |
| *C07C 215/40* | (2006.01) | |
| *C07D 295/088* | (2006.01) | |

(52) U.S. Cl.
CPC .......... *C07D 413/10* (2013.01); *A61K 31/4245* (2013.01); *C07C 213/08* (2013.01); *C07C 215/08* (2013.01); *C07C 215/40* (2013.01); *C07D 295/088* (2013.01)

(58) Field of Classification Search
CPC ...................................................... C07D 413/10
See application file for complete search history.

(56) References Cited

U.S. PATENT DOCUMENTS

| 5,243,054 A | 9/1993 | Naka et al. |
|---|---|---|
| 2005/0187269 A1 | 8/2005 | Kuroita et al. |

FOREIGN PATENT DOCUMENTS

| CN | 100503605 C | 6/2009 |
|---|---|---|
| CN | 101921264 A | 12/2010 |
| CN | 101381366 B | 6/2011 |
| EP | 0520423 A2 | 12/1992 |
| EP | 1452176 A1 | 9/2004 |
| WO | 2006038722 A1 | 4/2006 |
| WO | 2010075347 A2 | 7/2010 |
| WO | 2011063764 A1 | 6/2011 |

OTHER PUBLICATIONS

Childs et al. Molecular Pharmaceutics 2007, 4, 323-338.*
Encyclopedia Britannica, Entry for "Molecule," obtained from http://www.britannica.com/EBchecked/topic/388236/molecule on May 16, 2015.*
Int'l Search Report issued Apr. 19, 2012 in Int'l Application No. PCT/CN2012/070219.
White et al, "Effects of the Angiotensin Receptor Blocker Azilsartan Medoxomil Versus Olmesartan and Valsartan on Ambulatory and Clinic Blood Pressure in Patients With Stages 1 and 2 Hypertension," Hypertension, vol. 57, pp. 413-420 (Jan. 31, 2011).

* cited by examiner

*Primary Examiner* — Matthew Coughlin
(74) *Attorney, Agent, or Firm* — Panitch Schwarze Belisario & Nadel LLP (57) ABSTRACT

Disclosed are organic amine salts of azilsartan, a preparation method and use thereof. In particular, disclosed are organic amine salts of azilsartan, their preparation method, the pharmaceutical composition comprising the compound in a therapeutically effective quantity, and their use for the manufacture of antihypertensive medicaments.

13 Claims, 2 Drawing Sheets

ORGANIC AMINE SALTS OF AZILSARTAN, PREPARATION METHOD AND USE THEREOF

FIELD OF THE INVENTION

The present invention relates to organic amine salts of Azilsartan, a preparation method thereof, and the pharmaceutical composition comprising a therapeutically effective amount thereof, and their use for the preparation of antihypertensive medicaments as well.

BACKGROUND OF THE INVENTION

Hypertension is a common cardiovascular disease, the main clinical syndrome of which is the arterial pressure is elevated persistently, and it often causes lesions of the heart, brain, kidneys and other vital organs and the corresponding consequences. China is one of the countries affected by hypertension in the world. In the past few decades, the estimated number adults with hypertension has increased from 30 million in 1960 to 59 million in 1980, and reached to 94 million people in 1991. The number is more than 200 million currently. Among the 3 million cardiovascular patients that die every year, 50% are associated with hypertension. In the United States, ⅓ of adults are suffering from hypertension. It is extremely urgent to develop effective antihypertensive drugs with less adverse reactions.

According to the mechanism of the drug, conventional antihypertensive drugs can be classified into central antihypertensive drugs, ganglion blockers, sympathetic nerve endings inhibitors, adrenergic blockers, vasodilators, diuretics, angiotensin converting enzyme inhibitors (ACEI), angiotensin receptor antagonists. Renin-angiotensin system (RAS) is a group of hormones or precursors interacting or regulating with each other secreted by kidney and liver, including renin, angiotensinogen, angiotensin I (Ang I), angiotensin II (Ang II), angiotensin-converting enzyme (ACE) and angiotensin receptor etc., in which Ang II is one of the strongest vasoconstrictors, having numerous biological activities.

Azilsartan medoxomil (the structure of formula A) is an angiotensin II receptor antagonist drug for treating hypertension developed by Takeda, which belongs to angiotensin II receptor antagonist drug (Sartans). Azilsartan medoxomil potassium salt, Edabi® as the trade name, was approved by the FDA. This drug is an oral medicament which can be used alone or in combination with other antihypertensive agents for the treatment of hypertension and related complications. Azilsartan medoxomil has a more significant effect in lowering blood pressure. Compared with losartan and olmesartan medoxomil, Azilsartan medoxomil is more efficient in reducing blood pressure (WHITE W B. Effects of the angiotensin receptor blocker azilsartan medoxomil versus olmesartan and valsartan on ambulatory and clinic blood pressure in patients with stages 1 and hypertension J. Hypertension, 2011, 57(3): 413-420). Azilsartan medoxomil is a pro-drug, which can be rapidly hydrolyzed into Azilsartan and take action during absorption in the gastrointestinal tract. Azilsartan (the structure of formula B), the chemical name of which is 1-[[2'-(4,5-dihydro-5-oxo-1,2,4-oxadiazol-3-yl) [1,1'-biphenyl]-4-yl] methyl]-2-ethoxy-1H-benzimidazol-7-carboxylic acid, decreases blood pressure by selectively blocking the binding of angiotensin II to vascular smooth muscle AT1 receptor to block the vasoconstrictive effect of angiotensin II in vivo.

Formula A

Formula B

EP1992110668, U.S. Pat. No. 5,243,054A, and US20050187269 disclose the preparation method of Azilsartan and its analogues; Chinese patent CN100503605C discloses Azilsartan medoxomil potassium salt and the preparation and pharmacodynamic effect thereof; WO2010075347 discloses the pharmaceutical application and pharmacological activity of Azilsartan medoxomil and Azilsartan medoxomil potassium salt; CN101381366B discloses Azilsartan and Azilsartan medoxomil potassium salt.

However, subsequent research indicates that as there is a carboxyl group in the molecular structure of the direct active ingredient Azilsartan, the in vivo absorption is poor and it affects the efficacy of the drug, so Azilsartan is not easy to prepare into pharmaceutical dosage forms. In order to improve the bioavailability, Azilsartan has to be prepared into an ester by chemical modification, i.e. Azilsartan medoxomil, but its bioavailability is still not satisfied and its molecular structure becomes complex by such modification, which increases difficulty in synthesis and cost of production.

SUMMARY OF THE INVENTION

According to the research, the present invention proves that the salts formed by Azilsartan and organic amines have better pharmacokinetic parameters, higher bioavailability, lower drug toxicity, and the salts are more suitable for conventional preparation process.

The object of the present invention is to provide organic amine salts of Azilsartan, wherein the ratio of Azilsartan to organic amines is m:1, in which m is an integer selected from 2 to 10, and preferably m is 2.

Preferably, the organic amine salts of Azilsartan exist in the form of a single molecule or a complex. Said complex form is a molecular state well known by one skilled in the art, which commonly refers to (but is not limited to) a binding state formed by intermolecular interaction force, such as complex (composite) state formed by intermolecular force including hydrogen bond type, ionic bond type, charge transfer type and Van der Waals-type; complexing state formed by the non-covalent bond; and covalent conjugate formed by covalent bond.

Preferably, said organic amine is selected from the group consisting of methylamine, dimethylamine, trimethylamine, ethylamine, diethylamine, triethylamine, ethanolamine, piperazidine, dibenzyl ethylenediamine, meglumine, tromethamine, tetramethyl quaternary ammonium, tetraethyl quaternary ammonium or choline.

Preferably, said organic amine salt of Azilsartan has the structure of formula (I) or (II), wherein M is an organic amine selected from the group consisting of methylamine, dimethylamine, trimethylamine, ethylamine, diethylamine, triethylamine, ethanolamine, piperazidine, dibenzyl ethylenediamine, meglumine, tromethamine, tetramethyl quaternary ammonium, tetraethyl quaternary ammonium or choline.

(I)

(II)

(n is an integer greater than 1)

Preferably, the structure of said organic amine salt of Azilsartan is shown as formula (III) or (IV):

(III)

(IV)

(n is an integer greater than 1)

The present invention also provides the process for preparing compounds above, which comprises adding the acid form of Azilsartan and organic amine into alcoholic organic solvents respectively to obtain corresponding salts at room temperature or under heating, preferably said process is reacted under anhydrous conditions.

When the organic amine is choline, choline alcohol solution is preferably added when preparing corresponding Azilsartan choline salt, more preferably the concentration of said choline alcohol solution is 45%, even more preferably the molar ratio of said Azilsartan to choline is 1:1 to 2:1.

When the organic amine is selected from the group consisting of methylamine, dimethylamine, trimethylamine, ethylamine, diethylamine, triethylamine, ethanolamine, piperazidine, dibenzyl ethylenediamine, meglumine, tromethamine, tetramethyl quaternary ammonium or tetraethyl quaternary ammonium, preferably, when preparing corresponding Azilsartan organic amine salts, the molar ratio of Azilsartan to organic amine added in the alcoholic organic solvent is 2:1.

Said alcoholic organic solvent is selected from the group consisting of methanol, ethanol, propanol or isopropanol.

The present invention also provides a pharmaceutical composition for use in the treatment of hypertension, comprising a therapeutically effective amount of organic amine salts of Azilsartan as an active ingredient and pharmaceutically acceptable carriers.

Furthermore, the present invention provides the use of the organic amine salts of Azilsartan or its pharmaceutical composition in the preparation of antihypertensive medicaments.

In the preparation process of pharmaceutical compositions, it is important to prepare the drug into an appropriate convenient form, which is not only in view of commercially available preparation methods but also in view of preparing the pharmaceutical dosage forms containing the active compounds.

Moreover, it is important to provide a reliable, reproducible and constant drug plasma concentration curve after administering to a subject.

Other important factors include chemical durability, solid-state stability and storage life of the active ingredient. The drugs and the compositions containing the same should be preferably stored for a relatively long time with no obvious change in physical and chemical properties of their active ingredients, such as chemical composition, density, hygroscopicity and solubility.

Moreover, it is also important to provide the drug as pure as possible.

The person skilled in the art will understand that typically, if a drug can be obtained in a stable form, the drug can provide the following advantages: convenient handling, easy to be prepared into appropriate drug dosage forms and having reliable solubility.

An effective amount of the active ingredient is intended to be an effective nontoxic dosage, which preferably is selected from the range of 0.001 to 100 mg/kg of the total weight, and more preferably 0.001 to 50 mg/kg. When treating a subject in need of organic amine salt of Azilsartan, the administration route is preferably oral or parenteral, including topical, rectal, transdermal administration forms, injection or continuous infusion. An oral dosage unit for human administration preferably contains from 0.05 to 3500 mg of active ingredient, and most preferably from 0.5 to 1000 mg of active ingredient. Oral administration with lower dosage is more preferred. However, parenteral administration with high dosage also can be used when safe and convenient for the patient. The above dosage relates to the preferred amount of the active ingredient counted as the free acid.

It will be understood by one skilled in the art that the optimal quantity and period of dosage unit of the active ingredient for each individual will depend on the nature and extent of the disease, the dosage form, route and site of administration, and the conditions of the particular patient to be treated, and such optimums can be determined by conventional techniques. It will also be appreciated by one skilled in the art that the optimal course of treatment, i.e., the number of dosages of the active ingredient given per day for a defined number of days, can be determined by those skilled in the art by conventional tests.

The present compounds can be administrated orally or parenterally, and can be prepared into a tablet, pill, powder or granule for different administration routes. In these solid formulations, the active ingredient is mixed with at least one kind of inert diluent. According to conventional processes, an oral formulation also comprises substances other than inert diluent such as lubricants, glidants and antioxidants. In the case of a capsule, tablet and pill, the formulation contains buffering agent. Tablets and pills also can be made into sustained-release dosage form.

Although a non-aqueous emulsion can be used, the parenteral formulation of the present invention contains sterile aqueous solution. These formulations also contain an adjuvant, such as a preservative, wetting agent, penetrating agent, buffering agent, emulsion and dispersant. The composition is sterilized by a bacteria retaining filter, sterilizing agent, irradiation or heating.

Compared with Azilsartan and its ester, organic amine salts of Azilsartan of the present invention mainly have the following advantages:

1) The solubility of the salts of the present invention in conventional solvent is increased significantly, and it is suitable to be prepared into conventional formulations.

2) The salts of the present invention have better formulation application value.

3) The salts of the present invention have better bioavailability and better therapeutic effect.

4) The salts of the present invention have lower toxicity.

5) The process for preparation of the salts of the present invention has the advantages of high yield, high purity, quick, convenience and low cost, wherein ethanolamine salt and choline salt are more advantageous in process routes and can directly be precipitated into crystal form.

DETAILED DESCRIPTION OF THE INVENTION

Example 1

Azilsartan and Choline was Salified in a Molar Ratio of 1:1

Azilsartan (20.00 g, 0.0439 mol) was added into methanol (600.0 ml). The solution was supplemented with 46% of choline aqueous solution (11.80 g, 0.0439 mol) and stirred until clear. The reaction mixture was concentrated under reduced pressure. Isopropyl ether (100.0 ml) was added to the residue and the mixture was stirred to crystallization. After filtration and drying under vacuum, 18 g of white solid were obtained.

$^1$H NMR (DMSO-d6) δ: 1.32 (t, 3H, $CH_3$), 3.30 (s, 9H), 3.43 (t, 2H, $CH_2$), 3.97 (t, 2H, $CH_2$), 4.29 (q, 2H, $CH_2$), 5.46 (s, 2H, $CH_2$), 7.29~7.87 (m, 11H), 11.21 (br, 2H, NH, OH). Elemental analysis (%): C, 64.30; H, 6.02; N, 12.49.

Example 2

Azilsartan and Choline were Salified in a Molar Ratio of 2:1

Azilsartan (10.00 g, 0.022 mol) and ethanol (100.0 ml) were added into a reaction flask and heated to reflux. The mixture was supplemented with 45% of choline-methanol solution (5.90 g, 0.022 mol) and stirred for 3 hours at the same temperature until the mixture turned into a clear solution. The reaction mixture was cooled to room temperature and stirred to crystallization. After filtration and drying under vacuum, 6.80 g of white solid were obtained.

$^1$H NMR (DMSO-d6) δ: 1.38 (t, 6H, $CH_3$), 3.09 (s, 9H), 3.39 (t, 2H, $CH_2$), 3.82 (t, 2H, $CH_2$), 4.58 (q, 4H, $CH_2$), 5.69 (s, 4H, $CH_2$), 7.05~7.61 (m, 22H), 11.07 (br, 4H, NH, OH, $CO_2H$). Elemental analysis (%): C, 65.22; H, 5.42; N, 12.23.

Example 3

Azilsartan and Ethanolamine were Salified in a Molar Ratio of 1:1

Azilsartan (10.00 g, 0.0219 mol) was added into methanol (300.0 ml). The solution was supplemented with ethanolamine (1.34 g, 0.0219 mol) and stirred until clear. The reaction mixture was concentrated under reduced pressure. Isopropyl ether (100 ml) was added to the residue and the mixture was stirred to crystallization. After filtration and drying under vacuum, 10.30 g of white solid were obtained.

$^1$H NMR (DMSO-d6) δ: 1.30 (t, 3H, $CH_3$), 3.52 (t, 2H, $CH_2$), 4.27 (t, 2H, $CH_2$), 4.29 (q, 2H, $CH_2$), 5.52 (s, 2H, $CH_2$), 7.26~7.89 (m, 11H), 11.32 (br, 5H, NH, OH, $NH_3$). Elemental analysis (%): C, 62.59; H, 5.32; N, 13.54.

Example 4

Azilsartan and Ethanolamine was Salified in a Molar Ratio of 2:1

Azilsartan (10.00 g, 0.0219 mol) was added into methanol (300.0 ml). The solution was supplemented with ethanolamine (0.67 g, 0.0110 mol) and stirred until clear. The reaction mixture was concentrated under reduced pressure. The isopropyl ether (100 ml) was added to the residue and the mixture was stirred to crystallization. After filtration and drying under vacuum, 8.93 g of white solid were obtained.

$^1$H NMR (DMSO-d6) δ: 1.33 (t, 6H, $CH_3$), 3.09 (t, 2H, $CH_2$), 3.60 (t, 2H, $CH_2$), 4.30 (q, 4H, $CH_2$), 5.46 (s, 4H, $CH_2$), 7.28~7.93 (m, 22H), 11.0~13.0 (br, 7H, NH, $CO_2H$, OH). Elemental analysis (%): C, 64.07; H, 4.79; N, 13.12.

Example 5

Azilsartan and Piperazidine was Salified in a Molar Ratio of 2:1

Azilsartan (10.00 g, 0.0219 mol) was added into methanol (300.0 ml). The solution was supplemented with piperazidine (0.94 g, 0.0109 mol) and stirred until clear. The reaction mixture was concentrated under reduced pressure. Isopropyl ether (100 ml) was added to the residue and the mixture was stirred to crystallization. After filtration and drying under vacuum, 9.45 g of white solid were obtained.

$^1$H NMR (DMSO-d6) δ: 1.34 (t, 6H, $CH_3$), 2.68 (s, 8H, $CH_2$), 4.31 (q, 4H, $CH_2$), 5.47 (s, 4H, $CH_2$), 7.27~7.92 (m, 22H), 11.20 (br, 6H, NH, $CO_2H$). Elemental analysis (%): C, 64.79; H, 5.12; N, 14.15.

Experimental Example 1

Solubility Test

| Sample | Methanol | Ethanol | Isopropyl ether | Ethyl acetate | Chloroform |
| --- | --- | --- | --- | --- | --- |
| Example 1 Compound | a little soluble (1:40) | slightly soluble (1:120) | almost insoluble | almost insoluble | almost insoluble |
| Example 2 Compound | a little soluble (1:80) | slightly soluble (1:200) | almost insoluble | almost insoluble | almost insoluble |
| Example 3 Compound | a little soluble (1:40) | slightly soluble (1:120) | almost insoluble | almost insoluble | almost insoluble |

Conclusion: The solubility of example 1 compound is comparable to the solubility of example 2 compound.

Moreover, "1:40" refers to 1 g of sample was dissolved in 40 ml of methanol at room temperature, the same as "1:80"; "1:120" refers to 1 g of sample was dissolved in 40 ml of ethanol at room temperature, the same as "1:200".

Experimental Example 2

Hygroscopicity Test

Experimental Methods:

1. A dried glass weighing bottle (Outer diameter 50 nm, height 15 nm) with a plug was put into an artificial climate box under the temperature of 25° C.±1° C. and relative humidity (RH) of 80%±2% the day before and then weighed precisely ($m_1$).

2. The testing sample was weighed precisely ($m_2$) and lain into the weighing bottle. The thickness of the test sample was about 1 mm.

3. The uncovered weighing bottle and its plug were placed under the above constant temperature and humidity conditions for 24 h.

4. The weighing bottle was covered and weighed precisely ($m_3$).

Calculation formula: Percent of weight increase=$(m_3-m_2)/(m_2-m_1)*100\%$

5. Definition of the weight increase of the hygroscopicity

Deliquescence: absorbing enough water to form liquid.

High hygroscopicity: the weight increase of the hygroscopicity is no less than 15%

Having hygroscopicity: the weight increase of the hygroscopicity is between 15% and 2%

Slight hygroscopicity: the weight increase of the hygroscopicity is between 2% and 0.2%

No or almost no hygroscopicity: the weight increase of the hygroscopicity is less than 0.2%

6. Test results

| Sample | Hygroscopicity | Conclusion (hygroscopic or not) |
|---|---|---|
| Example 1 Compound | 10.51% | Yes |
| Example 2 Compound | 0.02% | No |
| Example 3 Compound | 5.66% | Yes |
| Example 4 Compound | 0.08% | No |

Conclusion: The example 2 compound and the example 4 compound are both not hygroscopic and are suitable for the preparation of medicine formulations and are favorable for the stability of formulation.

Experimental Example 3

Drug Metabolism Test of Sprague Dawley (SD) Rats after Administration

Figure 1:
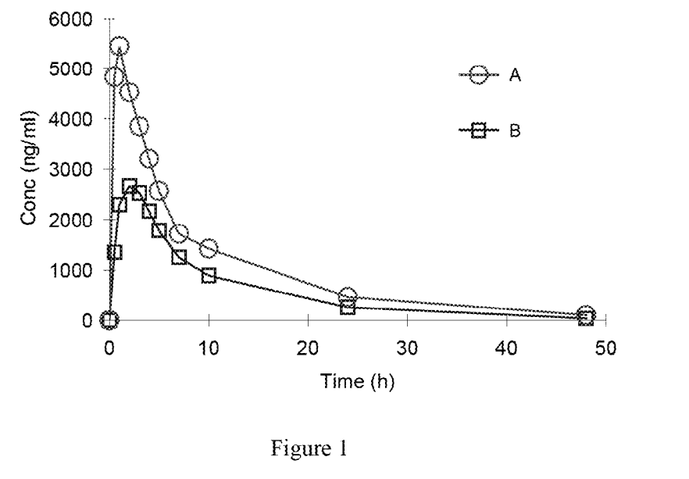
FIG. 1 shows the exposure level of Azilsartan in rats after administering 3.0 mg/kg of compound (A) prepared by example 2 and 3.58 mg/kg of Azilsartan medoxomil (B)
Figure 2:
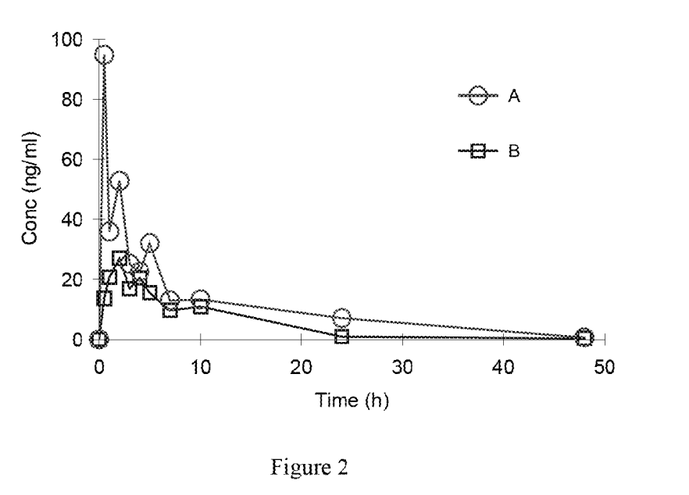
FIG. 2 shows the exposure level of M1 in rats after administering 3.0 mg/kg of compound (A) prepared by example 2 and 3.58 mg/kg of Azilsartan medoxomil (B)
Figure 3:
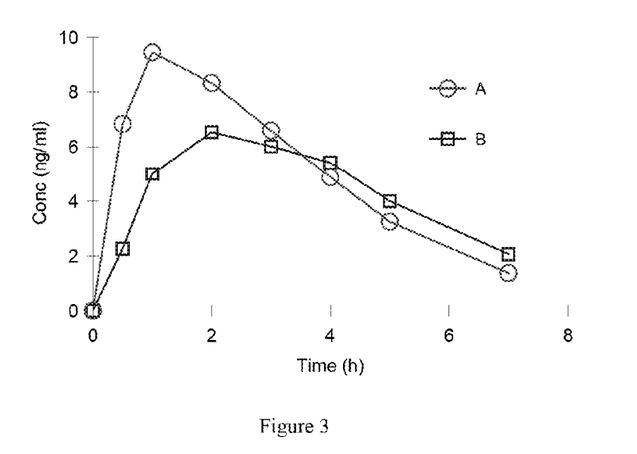
FIG. 3 shows the exposure level of M2 in rats after administering 3.0 mg/kg of compound (A) prepared by example 2 and 3.58 mg/kg Azilsartan medoxomil (B)

Twelve SD rats that weighed 200-250 g were randomly divided into two groups with each group having 6 rats, half male and half female. Equal molar amounts, 3 mg/kg of example 2 compound (Choline Azilsartan) or 3.58 mg/kg of Azilsartan kamedoxomil (API of Edarbi), were administered to adult rats by oral gavage. 0.5 ml blood were collected from orbit before administration and at 0.5, 1.0, 2.0, 3.0, 4.0, 5.0, 7.0, 10, 24 and 48 h after administration. Plasma concentration of Azilsartan (TAK-536), M1 (product of decarboxylation of Azilsartan) and M2 (product of O-dealkylation) was measured. The results are shown in the Table 1 and FIGS. 1-3 below.

Experimental Example 4

Antihypertensive Effect Test For Spontaneously Hypertensive (SHR) Rats 38 of 25 week old SHR male rats were randomly divided into 4 groups according to the initial blood pressure, with 6 for the control group (solvent) and 8 for other groups. 10 mg/kg of example 2 compound (Choline Azilsartan), example 4 compound (Azilsartan ethanolamine salts) and control (Azilsartan medoxomil potassium salt) were continuously administered, respectively. The solvent control group was administered solvent. The administration volume was 5 ml/kg and the period was 2 weeks.

Figure 4:
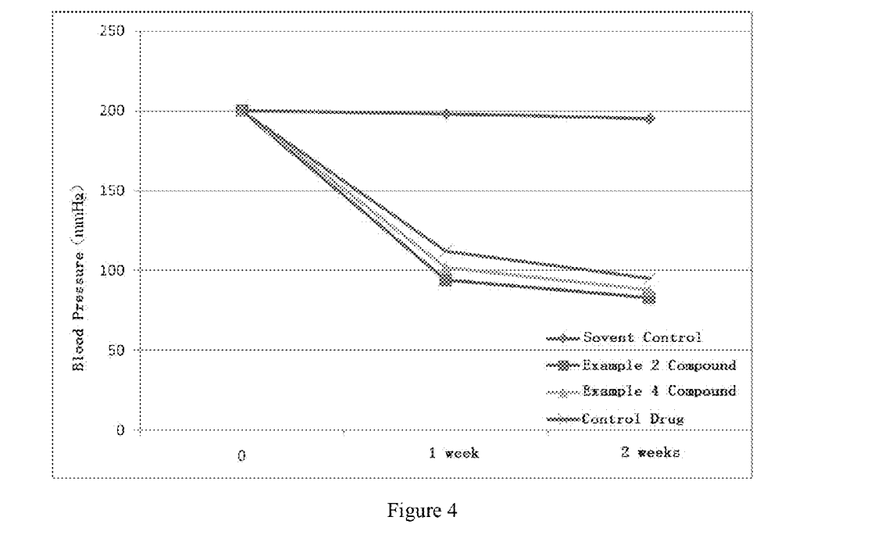
FIG. 4 shows the effect on the blood pressure of SHR rats after successionally administering the compound prepared by example 2 for two weeks.

It is shown in FIG. 4 that compared with solvent control, compounds of example 2 and example 4 can reduce the blood pressure of SHR rats significantly after continuously administering for one or two weeks. Under the same dosage, the effect of example 2 compound is optimal, the example 4 compound is less effective, but the two are both superior to the antihypertensive effect of control.

Experimental Example 5

The Effect on the Hypertension Rats Induced by Angiotensin II

1. Experimental Equipment and Other Materials
(1) Equipment
    DSI Remote Sensing Pressure Measuring System
    Blood Pressure Implants Type: TA11PA-C40, Data Sciences International.
    Blood Pressure Data Analysis Software: Ponemah Software 5.0, Data Sciences International.
    Alzet Micro Osmotic Pump: Alzet, model 2002, Alzet US.
(2) Test Sample and Agent
    The number of the test sample: HS-10149 (example 2 compound); batch: 20110324; provided by JIANGSU HANSOH PHARMACEUTICAL CO., LTD.; purity: 99.5%;
    physical state: white powder; storage condition: sealed, 4-8° C., dry, protection from light.
    Solvent: Ceolus; batch: B063; physical state: white powder; storage condition: sealed, room temperature, dry.

TABLE 1

The pharmacokinetic parameters in rats administered example 2 compound or Azilsartan kamedoxomil

| | | Dose (mg/kg) | T*$_{max}$ (h) | C$_{max}$ (ng/mL) | AUC$_{0-t}$ (h*ng/mL) | AUC$_{0-}$ (h*ng/mL) | MRT (h) | t$_{1/2}$ (h) |
|---|---|---|---|---|---|---|---|---|
| TAK-536 | Example 2 Compound | 3 | 1.0 | 5949 ± 2002 | 48527 ± 17029 | 50203 ± 18650 | 11.1 ± 3.0 | 9.65 ± 1.96 |
| | Azilsartan kamedoxomil | 3.58 | 2.0 | 3004.2 ± 656 | 28595 ± 6224 | 29097 ± 6289 | 10.5 ± 1.2 | 8.44 ± 0.76 |
| M1 | Example 2 Compound | 3 | 1.3 | 109 ± 85 | 490 ± 419 | 515 ± 419 | 10.4 ± 7.0 | 7.15 ± 3.44 |
| | Azilsartan kamedoxomil | 3.58 | 2.5 | 39.4 ± 28.2 | 231 ± 116 | 265 ± 110 | 15.3 ± 13.8 | 12.0 ± 12.9 |
| M2 | Example 2 Compound | 3 | 1.5 | 10.2 ± 5.5 | 36.9 ± 24.8 | 50.9 ± 26.1 | 4.82 ± 1.44 | 2.84 ± 0.89 |
| | Azilsartan kamedoxomil | 3.58 | 2.0 | 7.98 ± 2.37 | 31.3 ± 19.5 | 56.9 ± 20.4 | 6.58 ± 1.87 | 3.77 ± 1.55 |

*median

The results show that compared with the equal molar amount of Azilsartan ester, the C$_{max}$ and AUC of Azilsartan acid in the plasma is increased by 98% and 70% after administration of example 2 compound, and this difference has statistical significance. This illustrates that the exposure level of Azilsartan acid can be increased greatly by modification of Azilsartan ester into choline salts.

Angiotensin II: batch: 041M5062V; purity: ≥93%; storage condition: −20° C., protection from light;
Supplier: Sigma-Aldrich, Inc.

2. Preparation of Compounds
(1) Angiotensin II
    The dosage of angiotensin II was determined according to literature (Harrison-Bernard L M, Zhuo J, Kobori H, Ohishi M, Navar L G. Intrarenal A T (1) receptor and ACE binding in ANG II-induced hypertensive rats. *Am. J. Physiol. Renal Physiol.* 2002 January; 282(1):F19-25; Diz D I, Baer P G, Nasjletti A. Angiotensin II-induced hypertension in the rat. Effects on the plasma concentration, renal excretion, and tissue release of prostaglandins. *J. Clin. Invest.* 1983 August; 72(2):466-77.). Angiotensin II was precisely weighed and diluted with sterile saline up to a concentration of 14.4 mg/mL, then mixed slightly until clear and stored at −20° C. in the dark.

(2) Test Sample

HS-10149 suspension: the compounds were precisely weighed and diluted with 2% of Ceolus suspension in a gradient of 0.20 mg/ml, 0.06 mg/ml, 0.02 mg/ml, then the suspension was stirred until dissolution and stored at 4° C. in the dark. The sample was warmed to room temperature in advance before administration and mixed to uniform.

3. Experimental Animal

37 Sprague-Dawley rats (SHANGHAI SLAC LABORATORY ANIMAL CO. LTD), 17 female rats and 20 male rats, animal certificate number: 2007000524884, 2007000525715, 2007000526632.

4. Test Process (1) Hypertension Induction and Implant of Blood Pressure Implants The animals with required weight (female: 230-250 g, male: 200-220 g) were selected after adaptation for one week. The male rats were subjected to combined anesthesia of ketamine (44 mg/kg, im.) and 2% pentobarbital sodium solution (30 mg/kg, ip), and the female rates were narcotized with 2% pentobarbital sodium solution (40 mg/kg, ip). The implants were implanted on day 0 and the blood pressure was continuously monitored for 24 hours from the $7^{th}$ day after implantation of a micro osmotic pump. The animals with mean systolic blood pressure (MSBP) up to 140 mmHg over 24 hours were considered as standard screening animals. The qualified animals were used in the test and the unqualified animals were excluded.

(2) Groups

The qualified animals were divided into groups according to their MSBP over 24 hours, 8 animals for each group with half female and half male. 8 animals for each group met the requirement of statistical tests and the requirement of pharmacodynamics guiding principles.

(3) Administration

After grouping, the solvent control, low, middle and high dosage animal groups were intragastrically administered with 2% Ceolus, 0.1 mg/kg, 0.3 mg/kg and 1.0 mg/kg of HS-10149, respectively. The administration time was 10:00 and 10:30 a.m. and the administration volume was 5 mL/kg.

(4) Experimental Process Healthy animals were implanted with implants at day 0 and a micro osmotic pump was implanted subcutaneously at day 8. The blood pressure was monitored for 24 hours from the $15^{th}$ day and the animals with qualified blood pressure were selected to test. Positive drug or test sample was administered once at 10:00 a.m. on the $16^{th}$ day and the blood pressure was monitored after administration for 24 hours. At the end of the test, the animals were sacrificed by excessive carbon dioxide.

5. Handling and Analysis of Data

The data were recorded every 5 s automatically by the DSI remote sensing pressure measuring device. The mean value calculated within an hour as unit by the software was considered as initial data. $P<0.05$ shows there is a significant difference between medicated group and solvent control group, and **$P<0.05$ shows there is a high significant difference between medicated group and solvent control group.

6. Results (1) The Blood Pressure Elevation Effect

At the $6^{th}$ day after implant of micro osmotic pump filled with Angiotensin II, the ambulatory blood pressure of animals was monitored for 24 hours. The MSBP up to 140 mmHg over 24 hours is the standard of modeling success. The qualified animals were used in the test and the unqualified animals were excluded. 5 animals (4 male and 1 female) were excluded in this test. The mean value of MSBP of the qualified animals over 24 hours was 167 mmHg.

(2) The Effect of HS-10149 on the Blood Pressure of Model Animals

The data show that solvent does not influence the level of the blood pressure of the animals. The average blood pressure (the average value after administration over 23 hours) of the animals in three dosage groups (0.1 mg/kg, 0.3 mg/kg, 1.0 mg/kg) of HS-10149 was significantly reduced compared with that of solvent control group ($p<0.01$). The average ratio of reduction was 24.7%, 39.3%, 44.9% respectively. HS-10149 showed positive correlation of dosage and effect in the range of the dosage. All the average blood pressures between the test groups at 23, 13, 3 hours before administration and 1 hour after administration did not show a significant difference between groups ($p>0.05$). Compared with the solvent control group, the average blood pressures of three dosage groups (low, middle, and high dosage groups) of HS-10149 at 2, 7, 13, 18, and 23 hours after administration showed a high significant difference ($P<0.01$), and the average blood pressures of three dosage groups (low, middle, and high dosage groups) of HS-10149 at 23 hours after administration were greatly reduced. Therefore, the effect of HS-10149 after single administration can last about 23 hours.

Test Design

| Groups | Administration dosage(mg/kg) | Administration volume(ml/kg) | Administration concentration (mg/ml) | Numbers of the animal male | female |
|---|---|---|---|---|---|
| Solvent control | 0 | 5 | 0 | 4 | 4 |
| 0.1 mg/kg | 0.1 | 5 | 0.02 | 4 | 4 |
| 0.3 mg/kg | 0.3 | 5 | 0.06 | 4 | 4 |
| 1.0 mg/kg | 1.0 | 5 | 0.20 | 4 | 4 |

The solvent control is 2% Ceolus suspension.

Comparison of the average MBP over 23 hours before administration and 23 hours after administration (Mean±S.E., N=8)

| Groups | The average MBP over 23 hours before administration (mmHg) | The average MBP over 23 hours after administration (mmHg) |
| --- | --- | --- |
| Solvent control group | 145 ± 7 | 147 ± 5 |
| 0.1 mg/kg | 146 ± 5 | 110 ± 3** |
| 0.3 mg/kg | 145 ± 5 | 88 ± 7** |
| 1.0 mg/kg | 147 ± 5 | 81 ± 5** |

*P < 0.05,
**P < 0.01 vs. solvent control group

Comparison of Average Blood Pressure at Specific Time Before or after Administration (Mean±S.E., N=8)

| Groups | 23 hr before administration | 13 hr before administration | 3 hr before administration | 1 hr after administration | 2 hr after administration | 7 hr after administration | 13 hr after administration | 18 hr after administration | 23 hr after administration |
| --- | --- | --- | --- | --- | --- | --- | --- | --- | --- |
| Solvent control group | 140 ± 10 | 150 ± 7 | 133 ± 10 | 142 ± 5 | 137 ± 9 | 147 ± 10 | 159 ± 5 | 149 ± 7 | 141 ± 13 |
| 0.1 mg/kg | 142 ± 8 | 144 ± 7 | 128 ± 9 | 128 ± 8 | 102 ± 9** | 91 ± 5** | 110 ± 3** | 114 ± 3** | 109 ± 5** |
| 0.3 mg/kg | 147 ± 8 | 150 ± 6 | 124 ± 10 | 119 ± 11 | 83 ± 6** | 77 ± 4** | 91 ± 8** | 108 ± 10** | 93 ± 3** |
| 1.0 mg/kg | 146 ± 9 | 149 ± 7 | 129 ± 9 | 118 ± 6 | 85 ± 5** | 74 ± 4** | 76 ± 6** | 80 ± 5** | 81 ± 5** |

*P < 0.05,
**P < 0.01 vs. solvent control group

7. Conclusion

The test results show that HS-10149 shows a significant antihypertension effect in the hypertension rat models induced by angiotensin II. The drug effect and the dosage are positively coordinated between 0.1 mg/kg and 1.0 mg/kg. The minimum effective dose is 0.1 mg/kg and after administration for 23 hours, all three dosages show strong antihypertension effect.

Experimental Example 6

Acute Toxicity Test Research for Beagle Dog

Object: Approximate lethal dose method was introduced in the test to observe the acute toxicity response of the animals by intragastric administration of example 2 or Azilsartan medoxomil potassium salt to Beagle dogs to study the toxicity situation of example 2 after administration and compare the toxicity of example 2 and Azilsartan medoxomil potassium salt, which can provide reference confirmation for the evaluation of toxicity of example 2.

Method (approximate lethal dose method): 6 Beagle dogs were used, 3 for each of example 2 group and Azilsartan medoxomil potassium salt group. The administration dosage was 0.09, 0.13, 0.19, 0.28, 0.42, 0.63, 0.95, 1.42, 2.13, 3.20 $g \cdot kg^{-1}$ respectively, wherein 3.20 $g \cdot kg^{-1}$ was the maximum administration dosage (corresponding to 1081 times the given dosage for the clinical patient). The blood was collected before administration and on days 2, 7, and 14 after administration to test the corresponding biochemical indicators. Electrocardiogram, body weight, and body temperature were determined before administration and on days 7 and 14 after administration.

Test Results

The Azilsartan medoxomil potassium salt group: in the 3.20 $g \cdot kg^{-1}$ dosage group, on the day of administration the animals showed vomit, drooling, less moving; moving reduction on days 2~8, prostration on days 5~8, died on day 9; in the 2.13 $g \cdot kg^{-1}$ dosage group, on the day of administration the animals showed vomit, drooling, moving reduction; moving reduction on day 2 after administration, moving recovered on day 3 and no abnormality observed after day 3; in the 1.42 $g \cdot kg^{-1}$ dosage group, on the day of administration the animals showed vomit, less moving; moving reduction on day 2 after administration, moving recovered on day 3 and no abnormality observed after day 3.

The example 2 compound group: in the 3.20 $g \cdot kg^{-1}$ dosage group, on the day of administration the animals showed loose stools, liquid stools, vomit until the end of the observation and showed liquid stools, moving reduction on day 2 after administration, showed loose stools on day 3 and the moving recovered, the excreta recovered to normal on day 4 and no abnormality observed after that; in the 2.13 $g \cdot kg^{-1}$ dosage group, on the day of administration no abnormality was observed and the animals showed vomit, moving reduction on day 2 after administration, loose stools and moving recovered on day 3, and the excreta recovered to normal on day 4 and no abnormality observed after day 4; in the 1.42 $g \cdot kg^{-1}$ dosage group, on the day of administration the animals showed liquid stools and less moving, moving reduction on day 2 after administration, the moving recovered to normal on day 3 and no abnormality was observed after day 3.

The body weight of all of the animals in the group administered Azilsartan medoxomil potassium salt and example 2 decreased on day 7 after administration compared with pre-administration, and all of the surviving animals started to gain weight on day 14 after administration.

The body temperature of all of the animals in the group of Azilsartan medoxomil potassium salt and example 2 shows no abnormality on day 7 after administration and all of the surviving animals did not show abnormal body temperature on day 14 after administration.

Electrocardiogram and haematological indicators of all of the animals in the group administered Azilsartan medoxomil potassium salt and example 2 were not abnormal on day 7 after administration and all of the surviving animals did not show abnormal electrocardiogram and haematological indicators on day 14 after administration.

The systolic blood pressure and diastolic blood pressure of 5 animals in the group administered Azilsartan medoxomil potassium salt and example 2 were reduced more or less on day 2 after administration and all of the surviving animals did not show abnormal systolic blood pressure and diastolic blood pressure on day 14 after administration.

Azilsartan medoxomil potassium salt group: the dogs administered 3.20 $g \cdot kg^{-1}$ dosage showed increased ALT, AST, CK, CRE, UREA and UA on day 2 and day 7 after administration and died on day 9; the ALT, CRE, UREA and UA of the dogs of 2.13 g·kg$^{-1}$ dosage were increased significantly on day 2 after administration and the ALT, CK, CRE, and UA were increased significantly on day 7 and recovered to normal on day 14; the ALT, CRE, UA of the dogs of 1.42 g·kg$^{-1}$ dosage were increased significantly on day 2 after administration and CRE, UA were increased significantly on day 7 and recovered to normal on day 14, others did not show obvious anomaly.

Example 2 compound group: the CRE, UREA and UA of all the dogs administered Example 2 compound were increased significantly on day 2 after administration, the CRE and UA increased significantly on day 7 after administration, and they recovered to normal on day 14, the ALT of dogs with 3.20 g·kg$^{-1}$ dosage was increased on day 2 and recovered to normal on day 7, others did not show obvious anomaly.

The PT values of all the animals administered Azilsartan medoxomil potassium salt and example 2 compound were reduced significantly after administration compared to pre-administration. The Fib of 3.20 g·kg$^{-1}$ dosage of Azilsartan medoxomil potassium salt group was increased significantly on day 2 and day 7 after administration and the Fib of 2.13 g·kg$^{-1}$ dosage group was increased significantly on day 2 after administration. The Fib of 3.20 g·kg$^{-1}$ dosage of example 2 compound group was increased significantly on day 2 after administration. Others did not show obvious anomaly.

Azilsartan medoxomil potassium salt group: the animals of 3.20 g·kg$^{-1}$ dosage group died on day 9 after administration. The animals were dissected to show that the crissum was filthy and had blood excreta; the left lung lobe showed a black red color and the right lung lobe did not show obvious anomaly; the bottom of the stomach showed an off white verruca, the small intestine contents from middle jejunum to colon were reddish-brown and the color deepened with descent into the intestinal tract, the mucosa showed obvious anabrosis and sporadic dark red regions were present on the intestinal mucosa; other viscera did not show anomaly. The animals of 2.13 g·kg$^{-1}$ dosage group were dissected on day 15 to show that there were red dots on the bottom and cardia of the stomach, the mucosa was red and chyliform food were present in the stomach; other viscera did not show anomaly. The animals of 1.42 g·kg$^{-1}$ dosage group are dissected on day 15 to show that sporadic dark red regions are present on the mucosa of stomach and a few of chyliform food are present in the stomach; other viscera did not show anomalies.

Example 2 compound group: the animals of 3.20 g·kg$^{-1}$ dosage group were dissected on day 15; each tissue was dyed with htoxylin-eosin (HE) and observed under the light microscope; the animals did not show obvious anomalies. The animals of 2.13 g·kg$^{-1}$ dosage group were dissected on day 15 and showed that the stomach was filled and contained amounts of particle food; the cardiac mucosa was red and showed sporadic red dot; other viscera did not show anomalies. The animals of 1.42 g·kg$^{-1}$ dosage group were dissected and showed that the stomach was filled and contained amounts of particle food; the cardiac mucosa was red and showed sporadic red dot; other viscera did not show anomalies.

The anatomical observation records of the 3.20 g·kg$^{-1}$ dosage group of Azilsartan medoxomil potassium salt: each tissue was dyed with htoxylin-eosin (HE) and observed under the light microscope; the liver showed diffuse liver blood sinus expansion and part of the liver tissue autolysis; the lymphocyte in red pulp and white pulp of the spleen decreased significantly and the fibrous tissue in the red pulp had hyperplasia; the diffuse lung tissue had middle conges- tion edema; the renal tissue showed congestion and autolysis; the mucous epithelium of stomach was necrosed and the submucosa had edema; the fibroblast had hyperplasia and showed some new capillaries; the mucous epithelium of duodenum, jejunum, ileum, colon, cecum and rectum had focal necrosis or congestion and bleeding.

CONCLUSION

Under the conditions of the present experiment, the Beagle dog was intragastrically administered the example 2 compound or Azilsartan medoxomil potassium salt, the approximate lethal dose of the example 2 compound was more than 3.20 g·kg$^{-1}$ and the approximate lethal dose of Azilsartan medoxomil potassium salt was in the range of 2.13~3.20 g·kg$^{-1}$, therefore the acute toxicity of the example 2 compound is lower than that of Azilsartan medoxomil potassium salt.

What is claimed is:

1. An organic amine salt of Azilsartan, wherein the ratio of Azilsartan to organic amine is m:1 and m is an integer selected from 2 to 10.

2. The organic amine salt of Azilsartan according to claim 1, wherein the ratio of Azilsartan to organic amine is 2:1.

3. The organic amine salt of Azilsartan according to claim 1, wherein the organic amine is selected from the group consisting of methylamine, dimethylamine, trimethylamine, ethylamine, diethylamine, triethylamine, ethanolamine, piperazine, dibenzylethylenediamine, meglumine, tromethamine, tetramethyl quaternary ammonium, tetraethyl quaternary ammonium and choline.

4. The organic amine salt of Azilsartan according to claim 3, having formula (I) or (II), wherein M is an organic amine selected from the group consisting of methylamine, dimethylamine, trimethylamine, ethylamine, diethylamine, triethylamine, ethanolamine, piperazine, dibenzylethylenediamine, meglumine, tromethamine, tetramethyl quaternary ammonium, tetraethyl quaternary ammonium and choline,

(I)

(II)

and n is an integer greater than 1.

5. The organic amine salt of Azilsartan according to claim 3, having formula (III) or (IV):

wherein n is an integer greater than 1.

6. A process for preparing the organic amine salt of Azilsartan according to claim 1, comprising adding Azilsartan acid and an organic amine respectively into an alcoholic organic solvent at room temperature or under heating to obtain the salt.

7. A process for preparing the organic amine salt of Azilsartan of formula (III) according to claim 5, the process comprising adding Azilsartan acid and a choline alcohol solution into an alcoholic organic solvent.

8. The process according to claim 6, wherein the alcoholic organic solvent is selected from the group consisting of methanol, ethanol, propanol and isopropanol.

9. A pharmaceutical composition for the treatment of hypertension, comprising a therapeutically effective amount of the organic amine salt of Azilsartan according to claim 1 as an active ingredient and a pharmaceutically acceptable carrier.

10. The process according to claim 6, being conducted under an anhydrous condition.

11. The process according to claim 7, wherein the choline alcohol solution is a choline methanol solution containing 45% (by weight) choline.

12. The process according to claim 7, wherein the molar ratio of Azilsartan to choline is 1:1 to 2:1.

13. A method of treating hypertension in a subject in need thereof, comprising administering to the subject a pharmaceutical composition according to claim 9.

* * * * *